(12) United States Patent
Uitenbroek et al.

(10) Patent No.: US 6,682,512 B2
(45) Date of Patent: Jan. 27, 2004

(54) CONTINUOUS BIAXIALLY STRETCHABLE ABSORBENT WITH LOW TENSION

(75) Inventors: Duane Girard Uitenbroek, Little Chute, WI (US); Georgia Lynn Zehner, Larsen, WI (US); John Philip Vukos, Neenah, WI (US); Wendy Lynn Van Dyke, Appleton, WI (US); Paul Windsor Estey, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 217 days.

(21) Appl. No.: 10/034,681

(22) Filed: Dec. 18, 2001

(65) Prior Publication Data

US 2003/0120243 A1 Jun. 26, 2003

(51) Int. Cl.[7] ................................................ A61F 13/15
(52) U.S. Cl. ............................ 604/385.16; 604/385.22; 604/385.21; 604/385.27
(58) Field of Search ...................... 604/385.01, 385.16, 604/385.21, 385.22, 385.24, 385.27; 428/296.7, 297.4, 298.4, 311.71, 313.5; 442/328, 329, 333, 352, 375, 414, 415, 416

(56) References Cited

U.S. PATENT DOCUMENTS

| 4,100,324 A | 7/1978 | Anderson et al. | |
|---|---|---|---|
| 4,443,513 A | 4/1984 | Meitner et al. | |
| 4,469,734 A | 9/1984 | Minto et al. | |
| 4,663,220 A | 5/1987 | Wisneski et al. | |
| 4,704,116 A | 11/1987 | Enloe | |
| 4,741,949 A | * 5/1988 | Morman et al. | 442/329 |
| 4,775,579 A | * 10/1988 | Hagy et al. | 442/329 |
| 4,798,603 A | 1/1989 | Meyer et al. | |
| 4,810,556 A | 3/1989 | Kobayashi et al. | |
| 4,891,258 A | * 1/1990 | Fahrenkrug | 428/138 |
| 4,965,122 A | 10/1990 | Morman | |
| 4,981,747 A | 1/1991 | Morman | |
| 5,114,781 A | 5/1992 | Morman | |

(List continued on next page.)

FOREIGN PATENT DOCUMENTS

| EP | 0217032 A2 | 4/1987 | |
|---|---|---|---|
| EP | 630632 A2 | * 12/1994 | ........... A61F/13/15 |
| EP | 0701426 B1 | 3/1996 | |
| EP | 0788336 B1 | 8/1997 | |
| WO | WO 99/00095 A1 | 1/1999 | |

*Primary Examiner*—Weilun Lo
*Assistant Examiner*—Jacqueline Stephens
(74) *Attorney, Agent, or Firm*—Alyssa A. Dudkowski

(57) ABSTRACT

A dynamic-fitting absorbent article that includes a liquid impermeable outer cover (42), a liquid permeable bodyside liner (44) in superimposed relation to the outer cover (42) and a continuous elastic absorbent core (28) disposed between the outer cover (42) and the bodyside liner (44). The continuous elastic absorbent core (28) can extend from about 80 to about 400 percent upon application of a force of from about 60 to about 325 grams. The continuous elastic absorbent core (28) can have a tension reducing geometry in the crotch section of the article. Additionally, the continuous elastic absorbent core can have a dry tensile strength and a wet tensile strength that is at least 95% of the dry tensile strength.

58 Claims, 6 Drawing Sheets

U.S. PATENT DOCUMENTS

| | | | |
|---|---|---|---|
| 5,116,662 A | * 5/1992 | Morman | 428/198 |
| 5,176,668 A | 1/1993 | Bernardin | |
| 5,176,672 A | 1/1993 | Bruemmer et al. | |
| 5,192,606 A | 3/1993 | Proxmire et al. | |
| 5,226,992 A | 7/1993 | Morman | |
| 5,244,482 A | 9/1993 | Hassenboehler, Jr. et al. | |
| 5,358,500 A | 10/1994 | Lavon et al. | |
| 5,509,915 A | 4/1996 | Hanson et al. | |
| 5,560,878 A | * 10/1996 | Dragoo et al. | 264/115 |
| 5,611,790 A | 3/1997 | Osborn, III et al. | |
| 5,634,916 A | 6/1997 | Lavon et al. | |
| 5,643,242 A | 7/1997 | Lavon et al. | |
| 5,645,542 A | 7/1997 | Anjur et al. | |
| 5,669,897 A | 9/1997 | Lavon et al. | |
| 5,695,868 A | 12/1997 | McCormack | |
| 5,843,056 A | 12/1998 | Good et al. | |
| 5,846,232 A | 12/1998 | Serbiak et al. | |
| 5,853,405 A | 12/1998 | Suprise | |
| 5,883,028 A | 3/1999 | Morman et al. | |
| 5,964,743 A | * 10/1999 | Abuto et al. | 604/385.01 |
| 6,028,240 A | * 2/2000 | Wessel et al. | 604/358 |
| 6,049,023 A | 4/2000 | Blenke et al. | |
| 6,129,720 A | 10/2000 | Blenke et al. | |
| 6,149,934 A | 11/2000 | Krzysik et al. | |
| 6,193,701 B1 | 2/2001 | Van Gompel et al. | |
| 6,231,557 B1 | * 5/2001 | Krautkramer et al. | 604/385.16 |
| 6,315,765 B1 | 11/2001 | Datta et al. | |
| 6,362,389 B1 | 3/2002 | McDowall et al. | |

* cited by examiner

CONTINUOUS BIAXIALLY STRETCHABLE ABSORBENT WITH LOW TENSION

BACKGROUND OF THE INVENTION

The present invention is generally related to absorbent cores of absorbent articles where the absorbent core is formed from one continuous piece of material and where the absorbent core has elastic properties at low tensions.

Absorbent articles are used for a variety of applications including disposable diapers, training pants, disposable swim pants, adult incontinence garments, feminine hygiene products, wound dressings and nursing pads. The "workhorse" of an absorbent article is the absorbent core, which is the portion of the article that collects and retains a targeted exudate. This workhorse component can be thick and bulky relative to the other components of the article. Consequently, the absorbent core can reduce the flexibility and conformability of the article, thereby compromising the fit of the article on or against a wearer. "Good" fit is generally understood to correlate with good performance of the absorbent article.

The absorbent cores of the invention overcome deficiencies associated with known absorbent cores. Technical advances and the resulting improvements in the materials available for use in absorbent articles have led to better-fitting absorbent articles. For example, many years ago leg elastics were introduced to disposable diapers to improve the fit of the diaper around the legs of the wearer and to have a gasketing effect. Subsequently, extensibility and elasticity have been proposed for other components of disposable diapers and other absorbent articles. Not to be overlooked, various constructions and designs have been proposed for making the absorbent core extensible or elastic. Depending on the overall configuration or construction of an absorbent article, it can be beneficial to incorporate "stretch" into the absorbent core. Benefits include improvement of overall fit provided by virtue of the bulkiest component being more flexible and by virtue of not inhibiting any stretch or flexibility that may be possessed by other components of the absorbent article.

Generally speaking, when a material is "extensible", it is understood that the length or another dimension of the material can be increased with application of a force. The same can be said about a material that is described as being "elastic". The fundamental difference between "extensibility" and "elasticity" is the degree to which the material retracts once the force causing increase in length or other dimension is released. Extensible materials do not return to their original length or dimension as much as elastic materials. Extensible and elastic materials can be selected for almost every component of an absorbent article, including the absorbent core. Various considerations go into selecting such materials for a particular absorbent article design: the magnitude of elongation that the material is capable of; the force required to achieve that magnitude of elongation; the magnitude of retraction experienced by the material upon removal of the force and the speed with which the material retracts. Once the materials are selected for each component of the absorbent article, the materials must all work together to provide an article that is easy to apply, fits comfortably and performs its intended function.

The materials used to form the components of absorbent articles can be made extensible or elastic by building extension-capacity into the material (such as by necking or creping) or by incorporating an elastic material (such as LYCRA elastic strands) into the material. The actual components of an absorbent article (e.g. the outer cover, the liner, the containment flaps etc.) can also be made extensible or elastic by building extension-capacity into the component (such as by pleating or segmentation) or by incorporating an elastic material into the component. Generally speaking, materials and components are selected and designed to readily provide elongation or stretch without application of much force. Otherwise, the absorbent article would be difficult to use or uncomfortable to wear.

Attempts have been made to build extensibility or elasticity into the absorbent cores of absorbent articles. Those attempts have included both the building-in of extension capability and the incorporation of elastic materials. One way to "build-in" extension capability is to break the typical length of the absorbent core down into free-moving segments. A segmented absorbent core will typically have greater extensibility than a continuous piece or unitary absorbent core. For example, if a unitary absorbent core that is six inches in length is modified to be a segmented absorbent core having six, one inch segments, the segmented absorbent core will have more inherent extensibility that the continuous (six inch long) absorbent core. Broken down into independent-moving increments, the segmented core has increased freedom of movement over a unitary absorbent core; the segmented core can more readily respond to the relative motion of outer cover and liner components that may be extensible or elastic. Despite the advantages provided by the segmented absorbent core, the performance of the absorbent core, vis-à-vis the ability to rapidly distribute and retain fluids, may be compromised. The "breaks" or "discontinuities" between segments of the core may interrupt the wicking of fluids. Consequently, while segmentation is one approach to build-in extensibility or elasticity, segmentation has its drawbacks.

Elasticity has been built-in to absorbent cores through the incorporation of elastic materials into the traditional superabsorbent plus fluff (wood pulp) mixture. For example, elastic materials like LYCRA elastic strands, have been incorporated with superabsorbent and wood pulp to form elastic absorbent cores; the result is an absorbent structure having the ability to extend and retract. In some executions, relatively high quantities of elastic materials (e.g. greater than 30%) have been incorporated into the absorbent structure. While such absorbent cores have definitive elastic properties, it is possible that their absorptive capacity is diminished. Absorptive capacity is potentially diminished because superabsorbent and wood pulp are significantly replaced by elastic materials. A potential outcome is that the absorbent core must be oversized to have an absorptive capacity equal to a non-elastic core; the extra bulk counteracts the benefits of flexibility and conformability provided by an elastic core.

When elasticity is built-in to absorbent cores, it is known that is desirable to have the absorbent core extend at low tension. That is to say, the absorbent core extends or elongates with the application of minimal force (or tension). Typically, the absorbent core of an absorbent article forms the central portion of the article and the other components are built around the absorbent core. If the absorbent core requires the application of a relatively high force to extend it, any extensible or elastic capacity built-in to the other components will be dwarfed. Therefore, it is desirable to have the central and bulkiest component capable of elongating with the application of a relatively low force. In some applications, the absorbent core is capable of elongating under low tension and the absorbent core retracts almost completely (i.e. more than 90%) upon release of the force. While near total retraction is indicative of the elasticity of a component, near complete retraction may not be desirable. The force to elongate an absorbent article or components of an absorbent core is typically applied by the wearer or caregiver during the application of the article. It can be desirable for the article to form some "memory" of the elongation during application and to not completely or nearly completely retract. Some "set" (i.e. less than complete retraction) of the elastic components of the article can be desirable to provide customized fit of the article to an individual wearer. Less than total or near total retraction by the elastic components can also impart a more comfortable fit to the absorbent article because the elastic components are left with some "give" to conform to the shape of the individual wearer. Further, absorbent cores having high retraction may not possess elastic properties that are compatible with the other components of the absorbent article. Elastic absorbent cores that retract disproportionately to the other components of the absorbent article (i.e. the outer cover and liner) can be ill-fitting and have reduced performance. For example, if the absorbent core retracts more than the other components, the article will bunch-up and be uncomfortable to wear.

Ordinarily, the purpose of designing an absorbent core to be extensible or elastic is to create compatibility with other components of the absorbent articles into which extensibility or elasticity has been incorporated. That is, it is desirable for the absorbent core to be elongatable so that the stretch or elongation capability of the other components is not "tied-up" or diminished. While it is understood that stretchable materials provide better fitting absorbent articles, improved fit can not be achieved at the cost of a loss in performance. Therefore, it is important for stretchable absorbent cores to have performance at least equivalent to conventional, non-stretch absorbent cores. One aspect of article performance is the integrity of the absorbent core when wet or loaded.

Therefore, there remains a need for a stretchable absorbent core that is continuous so that the distribution and flow of targeted exudates is not inhibited. Further, there remains a need for an absorbent core possessing elastic properties without the significant replacement of absorptive materials within the core. Additionally, there remains a need for an absorbent core capable of elongating upon application of a low force (or tension) with managed retraction so as to not retract disportionately.

SUMMARY OF THE INVENTION

The present invention is directed in part to a dynamic-fitting absorbent article that includes a liquid impermeable outer cover, a liquid permeable bodyside liner and a continuous elastic absorbent core. The absorbent articles of the invention are dynamic-fitting to provide a conforming and comfortable fit to the wearer throughout the cycle of use of the absorbent article (i.e. providing a good fit at the time of application, providing a good fit as the article begins to be loaded and providing a good fit after the article has been completely loaded). The bodyside liner is provided in superimposed relation to the outer cover and the absorbent core is disposed between the outer cover and the bodyside liner. In one aspect of the present invention, the continuous elastic absorbent core can extend from about 80 to about 400 percent upon application or experience of a force of from about 60 to about 325 grams. Put differently, the continuous elastic absorbent core can have a tension of from about 60 to about 325 grams when extended by about 80% of its initial length. Additionally, the continuous absorbent core can have the same range of tension when extended by about 100, 200, 300 or 400% of an initial length (or other dimension). More desirably, the continuous elastic absorbent core can extend from about 80 to about 400 percent upon a force of from about 100 to about 250 grams. This is the same as saying that the continuous elastic absorbent core has a tension of from about 100 to about 250 grams when it is extended by 80 percent or any other percentage extension between about 80 and about 400 percent (e.g. 100, 200, 300 or 400 percent).

In another aspect, the continuous elastic absorbent core can recover no more than about 80% of an original dimension upon relaxation of the extension force. That is to say, the elastic absorbent core can retract only to within about 80% of the original dimension after the extension force is removed. Put differently, the post-extension dimension can be about 120% of the original dimension. For example, if the absorbent article (and therefore the absorbent core) is extended or elongated during application of the article, the absorbent core recovers no more than about 80% of its original length and/or width once the absorbent article is fastened or secured to the wearer.

In order to reduce the force or tension needed to fully elongate or extend the absorbent core, the continuous elastic absorbent core of the invention can have a tension reducing geometry in a crotch section of the absorbent core. Typical absorbent cores have an hourglass or rectangular shape that extends between a front waist section, a crotch section and a back waist section of the absorbent article (typically when the absorbent article is a disposable diaper, training pant, adult incontinence garment or feminine hygiene article). The tension in the crotch section of the absorbent core can be reduced by incorporating one or more slits or cuts into the absorbent core. The slits or cuts can be configured to reduce tension experienced during use by the crotch section of the absorbent core. The slit or slits can be oriented in the longitudinal or lateral direction of the absorbent core and can be from about 0.125 inches to about 2 inches depending on the size of the absorbent core and the selected configuration of slits. In another tension reducing geometry, the crotch section of the absorbent core can have a narrower width (or narrower dimension in the lateral direction) than the remainder of the absorbent core.

In another aspect, the continuous elastic absorbent cores of the invention can have a dry tensile strength, and a wet tensile strength that is at least 95% of the dry tensile strength. The tensile strength is a measurement of the force necessary to rupture or break the absorbent core. Typically, the wet tensile strength of an absorbent core is dramatically less than the dry tensile strength-if it is measurable at all (sometimes wet absorbent cores can not even be placed in the measurement device without falling apart). With the elastic absorbent cores of the invention, the wet tensile strength is very close to or even greater than the dry tensile strength.

Additionally, the continuous elastic absorbent cores of the invention can include from about 10 to about 20 weight percent of an elastic material that contributes or imparts the elastic capacity of the absorbent core. More specifically, the continuous elastic absorbent cores of the invention can include from about 13 to about 17 weight percent of an elastic material.

In addition to including continuous elastic absorbent cores, the dynamic-fitting absorbent articles of the invention can include a liquid impermeable outer cover that includes a biaxially stretchable material. A biaxially stretchable material is a material that extends in at least two directions such as the longitudinal and lateral directions of the outer cover and/or the absorbent article. A biaxially stretchable material is a material that is capable of extending upon application of a tensile force, and capable of retracting either partially or close to completely to its original dimension(s) upon removal of the force depending on the desired function of the absorbent article. In another aspect, the absorbent articles of the invention can include a liquid impermeable outer cover that includes a biaxially elastic material. A biaxially elastic material is a material that is capable of extending upon application of a force and that retracts to substantially to its original dimension(s) upon removal of the force. The dynamic-fitting absorbent articles of the invention can further include bodyside liners that include either biaxially stretchable materials and/or biaxially elastic materials. The stretchable and elastic properties of the outer cover and bodyside liner materials can be selected and interchanged depending on the desired function and performance of the absorbent article in conjunction with the absorbent core.

In another aspect, the present invention relates to a dynamic-fitting absorbent article that includes a liquid impermeable, biaxially stretchable outer cover; a liquid permeable, biaxially stretchable bodyside liner; and a continuous elastic absorbent core. The bodyside liner is in superimposed relation to the outer cover and the absorbent core is disposed between the outer cover and the bodyside liner. The continuous elastic absorbent core can extend from about 80 to about 400 percent upon application of a force of from about 60 to about 325 grams. Put differently, the continuous elastic absorbent core has a tension of from about 60 to about 325 grams when the core is extended a percentage, between about 80 and about 400 percent, of its initial length. More specifically, the absorbent core can extend from about 80 to about 400 percent upon a force of from about 100 to about 250 grams. This is the same as the elastic absorbent core having a tension of from about 100 to about 250 grams when the core is extended about 80 percent or any other percentage of its initial length up to about 400 percent. In another aspect, the continuous elastic absorbent core can recover no more than about 80% of an original dimension upon relaxation of the extension force. The original dimension can be in either a longitudinal or a lateral direction. Additionally, the absorbent core has a dry tensile strength and a wet tensile strength that is at least 95% of the dry tensile strength.

The present invention also relates to a dynamic-fitting absorbent article that includes a liquid impermeable outer cover, a liquid permeable bodyside liner and a continuous elastic absorbent core. The bodyside liner is in superimposed relation to the outer cover and the absorbent core is disposed between the outer cover and the bodyside liner. The continuous elastic absorbent core can recover less than about 80% of its original dimension upon relaxation of an extension force. That is to say, when the continuous elastic absorbent core is elongated, the absorbent core does not completely retract when the elongation force is removed. Further, the elastic absorbent core can include less than about 25% of an elastic material.

The elastic absorbent cores of this aspect of the invention are also capable of elongating upon application of a relatively low tension force. For example, the elastic absorbent cores can extend from about 80 to about 400 percent upon application of a force of from about 60 to about 325 grams. More specifically, the elastic absorbent cores can extend from about 80 to about 400 percent upon application of a force of from about 100 to about 250 grams. The benefits associated with form-fitting and body-conforming elastic absorbent cores are typically initially realized upon application of an article because absorbent articles are usually pulled and stretched during application to a wearer. In order to make application of such articles easy, it is desirable for the articles to be stretchable with the application of a low level of force. In order to provide a more comfortable fit to the wearer, it is desirable for the absorbent article to impart low tension during use; for example, it is desirable for the crotch section of the article to impart low tension during wear and loading. Therefore, the elastic absorbent cores of the invention can have a tension-reducing geometry in the crotch section. One example of a tension-reducing geometry is for the absorbent core to have one or more slits (oriented in either the longitudinal or lateral direction). The slits are capable of relieving localized forces and can aid in the distribution of forces across the entire absorbent core. Another tension-reducing geometry is for the elastic absorbent core to have a narrowed width in the crotch section. A narrowed width eliminates surplus material that can potentially bunch-up and pull other components of the article downward.

The continuous elastic absorbent cores of the invention can maintain their "wet" integrity and do not massively breakdown during loading or while the article is being worn. Maintenance of the overall integrity of the absorbent core improves the fit of the article during use and contributes to preventing leakage of exudates from the article. Therefore, the elastic absorbent cores can have a dry tensile strength and a wet tensile strength that is at least 95% of the dry tensile strength. Further to the purposes of reducing the tension of the absorbent articles and of not interfering with the absorptive and storage capabilities of the articles, the elastic absorbent cores of the invention have relatively low percentages of elastic materials to impart their flexibility. For example, the continuous elastic absorbent cores can include from about 10 to about 20 weight percent of an elastic material. More specifically, the elastic absorbent cores can include from about 13 to about 17 weight percent of an elastic material.

The articles of the invention can include a variety of outer cover and bodyside liner materials. For example, the outer cover material can have minimal elongation properties, can be stretchable in one or more directions and can be elastic in one or more directions. Similarly, the bodyside liner material can be essentially non-elongatable, can be stretchable in one or more directions and can be elastic in one or more directions. The outer cover and bodyside liner materials can be selected to have elongation properties that are appropriate for the desired function of the absorbent article in which they are used.

To maximize the fit range and conformability of the absorbent articles, it may be desirable for the article to include a liquid impermeable, biaxially stretchable outer cover, a liquid permeable, biaxially stretchable bodyside liner and a continuous elastic absorbent core disposed between the outer cover and the bodyside liner. The biaxially stretchable bodyside liner is in superimposed relation to the biaxially stretchable outer cover. The continuous elastic absorbent core can recover less than about 80% of an original dimension upon relaxation of an extension force and the absorbent core can include less than about 25% of an elastic material. The original dimension of the absorbent core is the length or width of the absorbent core prior to the application of an elongating force. The extension force is typically that force experienced by the absorbent core and the absorbent article during application of the article. The absorbent article desirably can be applied with a minimal effort to "activate" the inherent stretch properties of the article. In order to contribute to the low tension article, the elastic absorbent cores of the invention can extend from about 80 to about 400 percent upon application of a force of from about 60 to about 325 grams. More specifically, the elastic absorbent core can extend from about 80 to about 400 percent upon application of a force of from about 100 to about 250 grams. The continuous elastic absorbent core maintains its integrity after loading (when wet) and can have a dry tensile strength, and can have a wet tensile strength that is at least 95% of the dry tensile strength.

It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles and methods of the invention. Together with the description, the drawings serve to explain various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention is related to continuous elastic absorbent cores that can provide improved fit to absorbent articles throughout the full cycles of use of the absorbent articles. The elastic absorbent cores of the invention include an amount of elastic material that does not excessively interfere with the performance of the absorption function. The elastic absorbent cores of the invention also provide elongation without high tension; high tension, elastic components can make an absorbent article uncomfortable to wear and can affect the performance of the article. Additionally, the elastic absorbent cores of the invention can retract to within no more than about 80% of their original length (or width) after an elongation force is removed. Incomplete retraction can allow the absorbent core to form a more customized and conformable fit with the wearer of the absorbent article. Further, the continuous elastic absorbent cores of the invention can maintain their integrity when wet.

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The absorbent articles of the present invention will be described in terms of a disposable diaper article that is adapted to be worn by infants about the lower torso. It is understood that the articles of the present invention are equally adaptable for other types of absorbent articles such as adult incontinence products, training pants, disposable swim pants, feminine hygiene products and other personal care or health care garments.

Figure 1:
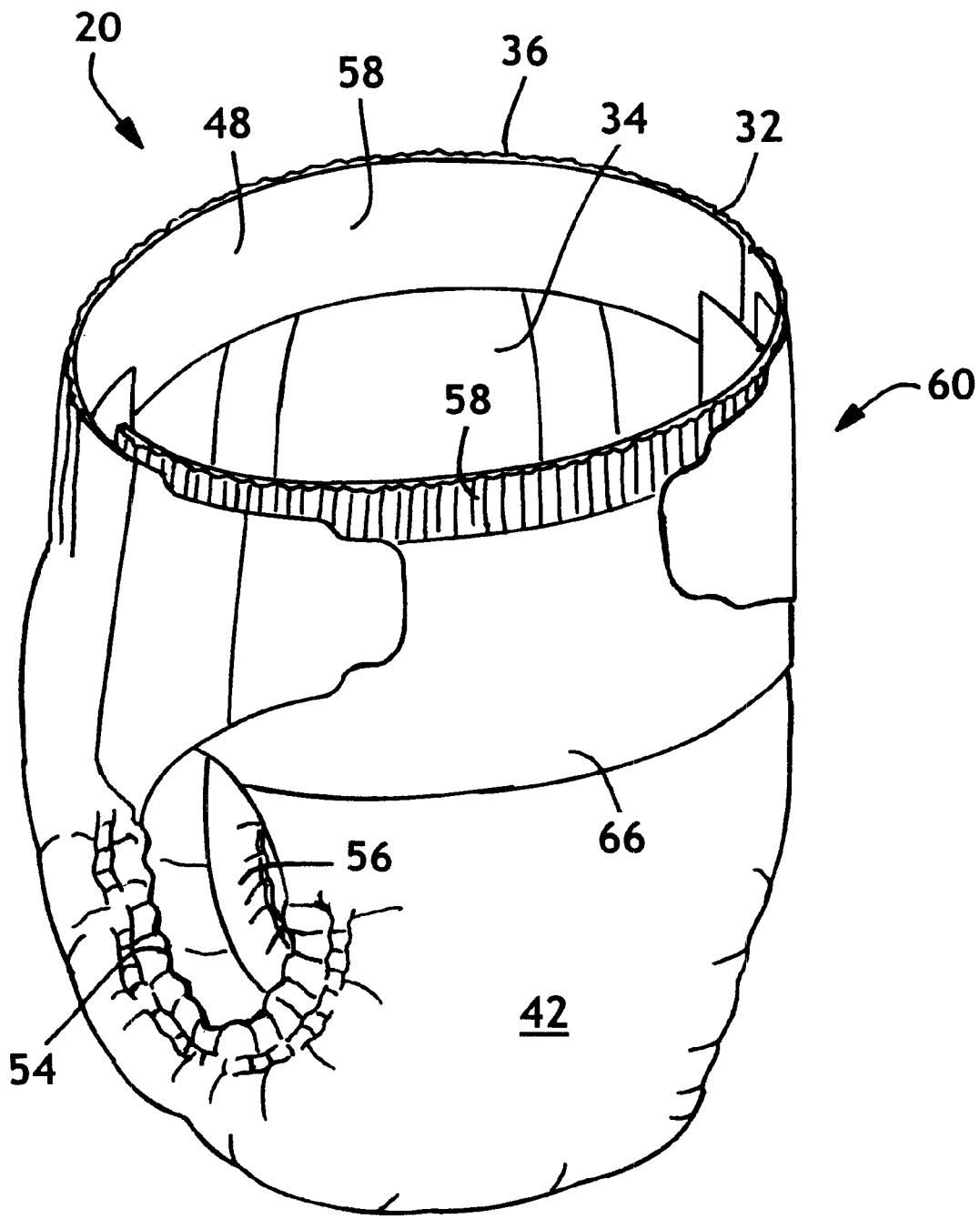
FIG. 1 representatively shows a perspective view of an example of an absorbent article of the present invention.
Figure 2:
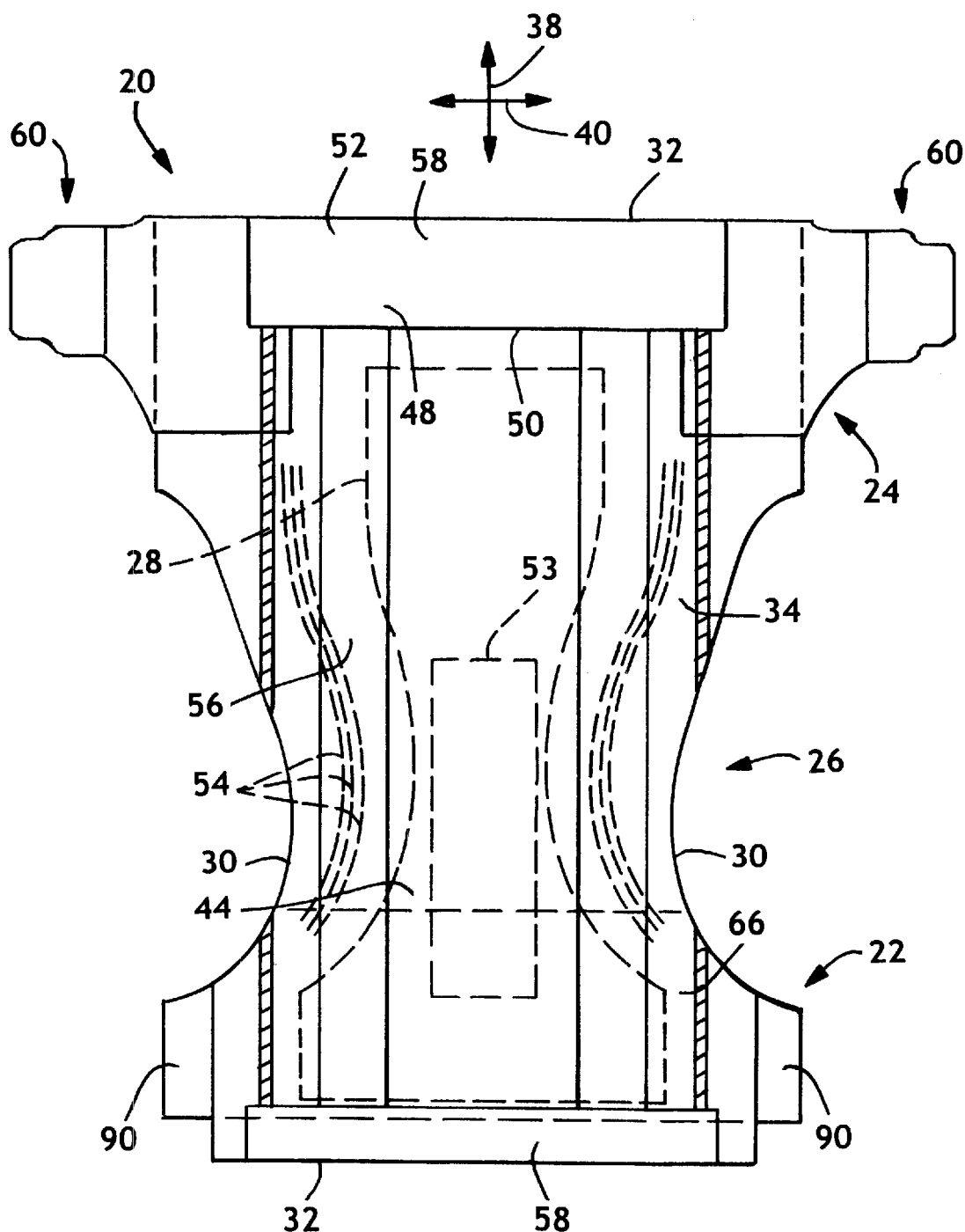
FIG. 2 representatively shows a plan view of the absorbent article of FIG. 1 in an unfastened, stretched and laid flat condition with the surface of the article which contacts the wearer's skin facing the viewer and with portions of the article partially cut away to show the underlying features.

FIG. 1 representatively illustrates an example of a refastenable disposable diaper, as generally indicated at 20, of the present invention. FIG. 2 representatively illustrates the refastenable diaper of FIG. 1 in an unfastened, stretched and laid flat configuration with the surface of the diaper adapted to contact the wearer's skin facing the viewer and with portions of the diaper partially cut away to show the underlying features. As illustrated in FIG. 2, the diaper 20 defines a front waist region 22, a back waist region 24, a crotch region 26 that extends between and connects the front and back waist regions 22 and 24, a longitudinal direction 38 and a lateral direction 40. The front waist region 22 includes the portion of the diaper 20 that, when worn, is positioned on the front of the wearer while the back waist region 24 includes the portion of the diaper 20 that, when worn, is positioned on the back of the wearer. The crotch region 26 of the diaper 20 includes the portion of the diaper 20 that, when worn, is positioned between the legs of the wearer and covers the lower torso of the wearer.

The diaper 20 defines a pair of laterally opposed side edges 30, a pair of longitudinally opposed waist edges 32, an interior surface 34 that is configured to contact the wearer, and an exterior surface 36 opposite the interior surface 34 that is configured to contact the wearer's clothing in use. The illustrated diaper 20 also includes a substantially liquid impermeable outer cover 42 and a liquid permeable bodyside liner 44 that can be connected to the outer cover 42 in a superposed relation. A continuous elastic absorbent core 28 is located between the outer cover 42 and the bodyside liner 44. The laterally opposed side edges 30 of the diaper 20 are generally defined by the side edges of the outer cover 42 that further define leg openings that may be curvilinear. The waist edges 32 of the diaper 20 are generally defined by the waist edges of the outer cover 42 and define a waist opening that is configured to encircle the waist of the wearer when worn. The continuous elastic absorbent core 28 is configured to contain and/or absorb body exudates discharged from the wearer. The diaper 20 may further include leg elastics 54, containment flaps 56 and waist elastics 58 as are known to those skilled in the art. It should be recognized that individual components of the diaper 20 may be optional depending upon the intended use of the diaper 20.

The diaper 20 can further include refastenable mechanical fasteners 60. The mechanical fasteners 60 releasably engage the opposed side edges 30 of the diaper 20 in the opposite waist regions. The mechanical fasteners 60 can include a variety of materials and surfaces known for mechanical engagement such as buttons, pins, snaps, adhesive tape fasteners, cohesives, mushroom-and-loop fasteners and hook and loop fasteners. Further, the disposable diaper 20 may include an attachment panel 66 located on the front or back waist region 22 and 24, opposite the fasteners 60 to which the fasteners 60 can be releasably engaged during use of the diaper 20.

The diaper 20 may be of various suitable shapes. For example, in the unfastened configuration as illustrated in FIG. 2, the diaper 20 may have an overall rectangular shape, T-shape or an approximately hourglass shape. In the shown embodiment, the diaper 20 has a generally I-shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the continuous elastic absorbent core 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the continuous elastic absorbent core 28 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the mechanical fasteners 60, may be assembled into the diaper 20 article by employing the above-identified attachment mechanisms. Desirably, the majority of the diaper components are assembled together using ultrasonic bonding techniques for reduced manufacturing cost.

The outer cover 42 of the diaper 20, as representatively illustrated in FIGS. 1–2, may suitably be composed of a material which is either liquid permeable or liquid impermeable. It is generally preferred that the outer cover 42 be formed from a material that is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). The materials of the outer cover 42 can be thermally or adhesively laminated together. Suitable laminate adhesives, which can be applied continuously or intermittently as beads, a spray, parallel swirls, or the like, can be obtained from Bostik-Findley, Inc., of Wauwatosa, Wis., U.S.A., or from National Starch and Chemical Company, Bridgewater, N.J., U.S.A. If it is desired to present the outer cover 42 with a more clothlike feeling, the outer cover 42 may be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may be thermally laminated thereto a spunbond web of polypropylene fibers. The polypropylene fibers can have a thickness of about 1.5 to 2.5 denier per filament, which nonwoven web has a basis weight of about 17 grams per square meter (0.5 ounce per square yard). The outer cover 42 may include bicomponent fibers such as polyethylene/polypropylene bicomponent fibers. Methods of forming such clothlike outer covers are known to those skilled in the art. The outer cover 42 may also be an extensible outer cover such as the outer covers described in U.S. patent application Ser. No. 09/563,417 filed on May 3, 2000 by Roessler et al. The disclosure of application Ser. No. 09/563,417 is intended to be incorporated herein to the extent it is consistent with the present disclosure. The outer cover 42 can also be a biaxially stretchable outer cover such as the outer covers described in U.S. patent application Ser. No. 09/698,512 filed on Oct. 27, 2000 by Vukos et al.

When materials are referred to as "biaxially stretchable", it means that the materials have stretchability in two directions perpendicular to one another, e.g. stretchability in a machine direction and in a cross direction, or in a longitudinal direction (front to back) and a lateral direction (side to side). Further, "stretchable" means that a material can be stretched, without breaking, by at least 50% (to at least 150% of its initial (unstretched) length) in at least one direction, suitably by at least 100% (to at least 200% of its initial length), desirably by at least 150% (to at least 250% of its initial length). The term "stretchable" includes elastic materials as well as materials that stretch but do not significantly retract. "Elastic" materials are understood to tend to retract more completely (closer to 100% of an original dimension), but do not have to retract 100%.

The outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a micro-porous "breathable" material which permits vapors to escape from the absorbent core 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8,1987 in the names of Taylor et al., the disclosures of which are hereby incorporated by reference. The outer cover 42 can also be embossed or otherwise provided with a matte finish to provide a more aesthetically pleasing appearance.

Suitable materials for a biaxially stretchable outer cover 42 include biaxially stretchable material and biaxially elastic stretchable material. One example of a suitable outer cover material can include a 0.3 osy polypropylene spunbond that is necked 60% in the lateral direction 40 and creped 60% in the longitudinal direction 38, laminated with 3 grams per square meter (gsm) Findley 2525A styrene-isoprene-styrene based adhesive to 8 gsm PEBAX 2533 film with 20% $TiO_2$ concentrate. The outer cover 42 can suitably be stretched, laterally and/or longitudinally, by at least 50% (to at least 150% of an initial (unstretched) width and/or length of the outer cover 42). More suitably, the outer cover 42 can be stretched, transversely and/or laterally, by at least 100% (to at least 200% of the unstretched width or length of the outer cover 42). Even more suitably, the outer cover 42 can be stretched, laterally and/or longitudinally, by at least 150% (to at least 250% of the unstretched width or length of the outer cover 42). Tension force in the outer cover 42 at 50% extension is suitably between 50 and 1000 grams, more suitably between 100 and 600 grams, as measured on a 3 inch (7.62 cm) wide piece of the outer cover material.

Another example of suitable material for forming a stretchable outer cover 42 is a thermoplastic nonwoven web, such as a spunbond thermoplastic nonwoven web made from a stretchable polymer and having a basis weight of about 1–100 grams per square meter (gsm), suitably about 5–50 gsm, more suitably 10–30 gsm. Suitable stretchable polymers for making the nonwoven web include certain flexible polyolefins, for example propylene-based polymers having both atactic and isotactic propylene groups in the main polypropylene chain. Flexible polyolefins (FPO's) are sold by the Rexene Corporation. Also included are heterophasic propylene-ethylene copolymers sold as "catalloys" by the Himont Corporation. Heterophasic polymers are reactor blends formed by adding different levels of propylene and ethylene at different stages in the reactor. Heterophasic polymers typically include about 10–90% by weight of a first polymer segment A, about 10–90% by weight of a second polymer segment B, and 0–20% by weight of a third polymer segment C. Polymer segment A is at least about 80% crystalline and includes about 90–100% by weight propylene, as a homopolymer or random copolymer with up to 10% by weight ethylene. Polymer segment B is less than about 50% crystalline, and includes about 30–70% by weight propylene randomly copolymerized with about 30–70% by weight ethylene. Optional polymer segment C contains about 80–100% by weight ethylene and 0–20% of randomly copolymerized propylene.

Other stretchable polymers can include very low density polyethylene (VLDPE), such as an ethylene-alpha olefin copolymer having a density less than about 0.900 grams/cm$^3$, preferably about 0.870–0.890 grams/cm$^3$. Preferred VLDPE's are single-site catalyzed. Other stretchable polymers can include random propylene-alpha olefin copolymers containing more than 10% by weight of a $C_2$ or $C_4$–$C_{12}$ comonomer, preferably about 15–85% by weight of the comonomer, with ethylene being a preferred comonomer.

When the outer cover 42 includes a biaxially stretchable material, the inner film layer can desirably be manufactured from a thin (1–50 microns, suitably 5–25 microns, more suitably 10–20 microns) plastic film, although other stretchable liquid impermeable materials may also be used. The film can contain a blend of a thermoplastic polymer and a 30–70% by weight of a particulate inorganic filler, such as calcium carbonate. The film can be oriented at least uniaxially to cause void formation around the filler particles, resulting in breathability. Suitable stretchable polymers for making the film include stretchable olefin polymers, such as an olefinic copolymer of polyethylene. More specifically, other stretchable polymers include diblock, triblock, tetrablock or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from KRATON Polymers, Inc., under the trade designation KRATON elastomeric resin; polyurethanes, including those available from E. I. du Pont de Nemours Co., under the trade name LYCRA polyurethane; polyamides, including polyether block amides available from Ato Chemical Company, under the trade name PEBAX polyether block amide; polyesters, such as those available from E. I. Du Pont de Nemours Co., under the trade name HYTREL polyester; and single-site or metallocene-catalyzed polyolefins having density less than about 0.91 grams/cc, available from Dow Chemical Co. under the trade name AFFINITY.

Additional suitable materials for a biaxially stretchable outer cover 42 can include a spunbonded laminate, a meltblown laminate, a spunbond-meltblown-spunbond laminate, or a stretch-bonded laminate (SBL) made using a stretchable polymer, as well as combinations thereof. A more specific example of a suitable liquid impermeable film for use as a liquid impermeable inner layer, or a single layer liquid impermeable stretchable outer cover 42, is a 0.02 millimeter polyethylene film commercially available from Pliant Corporation of Newport News, Va., U.S.A. If the stretchable outer cover 42 is a single layer of material, it can be embossed and/or matte finished to provide a more cloth-like appearance.

Another example of a suitable material for a biaxially stretchable outer cover 42 is a breathable elastic film/nonwoven laminate, described in U.S. Pat. No. 5,883,028, issued to Morman et al., herein incorporated by reference. Examples of materials having two-way stretchability and retractability are disclosed in U.S. Pat. No. 5,116,662 issued to Morman and U.S. Pat. No. 5,114,781 issued to Morman, both of which are hereby incorporated by reference. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The dynamic-fitting absorbent articles of the invention include a bodyside liner 44 in superimposed relation to the outer cover 42. The bodyside liner 44, as representatively illustrated in FIG. 2, suitably presents a bodyfacing surface that is compliant, soft feeling, and nonirritating to the wearer's skin. Further, the bodyside liner 44 may be less hydrophilic than the absorbent core 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent 28. The bodyside liner 44 can also be made from extensible materials as are described in U.S. patent application Ser. No. 09/563,417 filed on May 3, 2000 by Roessler et al. The bodyside liner 44 can also be made from biaxially stretchable materials as are described in U.S. patent application Ser. No. 09/698,512 filed on Oct. 27, 2000 by Vukos et al.

Various woven and nonwoven fabrics can be used for the bodyside liner 44. For example, the bodyside liner may be composed of a meltblown or spunbond web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In a particular embodiment of the present invention, the bodyside liner 44 is made from a nonwoven, spunbond, polypropylene fabric composed of about 2.8–3.2 denier fibers formed into a web having a basis weight of about 20 grams per square meter and a density of about 0.13 grams per cubic centimeter. The fabric may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, brush coating or similar techniques. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto that is configured to be transferred to the wearer's skin. Suitable compositions for application to the bodyside liner 44 are described in U.S. Pat. No. 6,149,934 that issued to Krzysik et al. on Nov. 21, 2000.

The body side liner 44 can be biaxially stretchable. It is desirable for the bodyside liner 44 to be biaxially stretchable when a biaxially stretchable outer cover 42 is used so that the bodyside liner 44 expands along with the biaxially stretchable outer cover 42. The bodyside liner 44 may be biaxially stretchable, or biaxially stretchable and retractable (i.e., elastic). The biaxially stretchable bodyside liner 44 can be manufactured from a wide selection of web materials, such as synthetic fibers (for example, polyester or polypropylene fibers), a combination of synthetic and natural fibers (examples of natural fibers including cotton fibers), porous foams, reticulated foams, apertured plastic films, or the like. The stretchable bodyside liner 44 can suitably be composed of a neck-stretched, spunbond web with KRATON G strands, such as 0.4 osy (60% neck-stretched) polypropylene spunbond laminated to 0.4 osy strands of KRATON MM G2760 with 12 strands per inch, which is stretched then allowed to retract. Other suitable materials may be extensible biaxially stretchable materials, such as a neck stretched/creped spunbond.

The dynamic-fitting absorbent articles of the invention can include a continuous elastic absorbent core 28 disposed between the outer cover 42 and the bodyside liner 44. The continuous elastic absorbent core 28 is discussed in detail herein. The dynamic-fitting absorbent articles of the invention can include additional components. For example, as representatively illustrated in FIGS. 1 and 2, the disposable diaper 20 may include a pair of containment flaps 56 that are configured to provide a barrier to the lateral flow of body exudates. The containment flaps 56 may be located along the laterally opposed side edges 30 of the diaper adjacent the side edges of the absorbent core 28. Each containment flap 56 typically defines an unattached edge that is configured to maintain an upright, perpendicular configuration in at least the crotch region 26 of the diaper 20 to form a seal against the wearer's body. The containment flaps 56 may extend longitudinally along the entire length of the absorbent core 28 or may only extend partially along the length of the absorbent core 28. When the containment flaps 56 are shorter in length than the absorbent core 28, the containment flaps 56 can be selectively positioned anywhere along the side edges 30 of diaper 20 in the crotch region 26. In a particular aspect of the invention, the containment flaps 56 extend along the entire length of the absorbent core 28 to better contain the body exudates. Such containment flaps 56 are generally well known to those skilled in the art. For example, suitable constructions and arrangements for containment flaps 56 are described in U.S. Pat. No. 4,704,96 issued Nov. 3, 1987, to K. Enloe, the disclosure of which is hereby incorporated by reference.

The diaper 20 of the different configurations of the present invention may further include elastics at the waist edges 32 and side edges 30 of the diaper 20 to further prevent leakage of body exudates and support the absorbent core 28. For example, as representatively illustrated in FIGS. 1–2, the diaper 20 of the present invention may include a pair of leg elastic members 54 that are connected to the laterally opposed side edges 30 of the diaper 20 in the crotch region 26. The diaper 20 may also include a pair of waist elastic members 58 that is connected to the longitudinally opposed waist edges 32 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material that are adhered to the outer cover 42 in a stretched position, or that are attached to the outer cover 42 while the outer cover is pleated, such that elastic constrictive forces are imparted to the outer cover 42. The leg elastics 54 may also include such materials as polyurethane, synthetic and natural rubber.

The diaper 20 of the different configurations of the present invention may further include a fit panel 48 superimposed adjacent to the waist edge 30 in at least one of the waist sections 22 and 24, to provide a more comfortable, contouring fit about the wearer. For example, as illustrated in FIG. 2, the diaper 20 may include a fit panel 48 superimposed adjacent the waist edge 32 on either the interior or exterior surface 34 and 36 of the diaper 20. Or there may be a fit panel located on both surfaces 34 and 36 of the diaper 20 simultaneously. The diaper may include a fit panel disposed in both waist sections 22 and 24, and desirably the diaper may include a fit panel in at least the rear waist section 24. Desirably, the fit panel is extensible or elastomeric. For example, as representatively illustrated in FIG. 2, the diaper 20 can include an elastomeric fit panel 48 on the interior surface 34 of the diaper 20 that is configured to elongate in the lateral direction 40 to provide an improved fit and appearance of the absorbent article about the wearer. This can be accomplished by providing a mechanism for the waist region to expand, thereby increasing the waist perimeter dimension to assist in applying the diaper 20 on the wearer. Desirably the elastomeric or extensible fit panel 48 allows the waist perimeter dimension to expand at least about 20 percent, more desirably at least about 40 percent and even more desirably at least about 50 percent. The fit panel 48 is further capable of initially providing a conforming fit about the wearer and maintaining such fit throughout the use of such article. The fit panel 48 can also be configured such that the absorbent core 28 has the ability to expand, contract and receive body exudates without adversely affecting the positioning of the fit panel 48 and the article about the waist of the wearer. Thus, with such a fit panel 48, movements of the wearer may move the absorbent but do not adversely affect the overall positioning and fit of the article on the wearer. Such improved fit can result in reduced leakage from the absorbent article and a more aesthetically pleasing appearance.

As representatively illustrated in FIG. 2, when the fit panel 48 is located on the interior surface 34, it may also extend beyond the side edges of the absorbent core 28 of the diaper 20 and be generally coterminous with the waist edge 32 of the diaper 20 in the respective waist section 22 or 24. When located on the interior surface 34 of the diaper 20, the fit panel 48 may define a free edge 50 that extends longitudinally inward towards the crotch region 26 of the diaper 20. In a particular embodiment the free edge 50 of the fit panel 48 is configured to remain at least partially unattached to the bodyside liner 44 of the diaper 20 when in use to allow the absorbent core 28 to move and expand to receive and contain body exudates. The unattached free edge 50 may also form a pocket between the fit panel 48 and the bodyside liner 44 that is configured to further contain body exudates. The free edge 50 of the fit panel 48 may be linear or curvilinear, such as concave, to better fit the wearer. The waist edge 52 of the fit panel 48 may also be curvilinear to better fit the wearer. Desirably, if the free edge 50 is curvilinear, the waist edge 52 is also curvilinear such that consecutive fit panels 48 for multiple articles nest within each other and can be provided from a continuous sheet of material. In such a configuration, the free edge 50 of the first fit panel corresponds to the waist edge 52 of the next fit panel to improve manufacturing and reduce waste.

The fit panel 48 as representatively illustrated in FIG. 2 can be provided in any suitable manner that provides the desired fit properties and performance. Desirably, the fit panel 48 can be an elastomeric material, or an extensible material. The materials may include a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220, issued May 5, 1987 to T. Wisneski et al., the disclosure of which has previously been incorporated by reference. Examples of composite fabrics comprising at least one layer of a non-woven material secured to a fibrous elastic layer are described in European Patent Application No. EP 090 010 published on Apr. 8, 1987 with the inventors listed as J. Taylor et al., the disclosure of which has previously been incorporated by reference. Examples of NBL materials are described in U.S. Pat. No. 5,226,992 issued Jul. 13, 1993 to Morman, the disclosure of which has previously been incorporated by reference.

Alternatively, the fit panel 48 may be provided by a substantially non-elastomeric material, such as polymer films, woven fabrics, non-woven fabrics, or similar materials such as described above as being suitable for the outer cover 42 or the bodyside liner 44. For example, the fit panel 48 may include a polyethylene film having a nonwoven web laminated to the outer surface thereof. The fit panel 48 may also be formed of a woven or nonwoven fibrous web layer that has been totally or partially constructed or treated to impart a desired level of liquid impermeability, or wettability and hydrophilicity. Still further, the fit panel 48 may optionally be composed of a micro-porous "breathable" material that permits vapors to escape from between the fit panel 48 and the bodyside liner 44 of the diaper 20.

The fit panel 48 of the different embodiments of the present invention may be attached to the diaper 20 in any suitable manner that provides the desired properties. For example, the fit panel 48 may be attached to the diaper using adhesive, ultrasonic, thermal bonding techniques and the like or combinations thereof. Absorbent articles including such a fit panel 48 and methods of making the same are further described in PCT Patent Application WO 97/48357 published Dec. 24, 1997 and entitled "ABSORBENT ARTICLE HAVING FIT PANEL", the disclosure of which is hereby incorporated by reference.

As previously described herein, the dynamic-fitting absorbent articles of the invention include a continuous elastic absorbent core 28. The absorbent cores 28 of the invention are configured to utilize extensible and stretchable materials to provide superior dynamic fit and comfort to the wearer of the article. The materials can be extensible or stretchable in one direction or they can be biaxially extensible or stretchable. As will be described in more detail, the absorbent structure can include a top and a bottom carrier layer and a surge layer 53. The absorbent core 28 can include a continuous coform layer and a retention layer. The continuous coform layer and the retention layer can both include traditional superabsorbent and pulp materials. A description of the method by which basic pulp is coformed can be found in U.S. Pat. No. 4,100,324 and a method by which pulp is coformed with particles can be found in U.S. Pat. No. 4,469,734.

The superabsorbent and pulp materials compose a matrix of hydrophilic fibers, such as a web of cellulosic fluff, mixed with particles of a high-absorbency material commonly known as superabsorbent material. For example, the absorbent core 28 (both the continuous coform and retention layers) can include a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 28 to better contain and absorb body exudates. The concentration of the superabsorbent particles may also vary through the thickness of the absorbent 28. Alternatively, the absorbent core 28 may include a laminate of fibrous webs and superabsorbent material or other suitable method for maintaining a superabsorbent material in a localized area.

The absorbent core 28 may have any of a number of shapes. For example, the absorbent may be rectangular, I-shaped, or T-shaped. It is generally preferred that the absorbent core 28 be narrow in the crotch region 26 of the diaper 20. It has been found that the absorbent core 28 of the present invention is particularly useful when the width dimension in the crotch region 26 is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent core 28 allows the absorbent core 28 to better fit between the legs of the wearer. The size and the absorbent capacity of the absorbent core 28 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and similar compounds. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent core 28 in an amount of from about 5 to about 90 weight percent based on total weight of the absorbent core 28.

The top and bottom carrier layers, the continuous coform layer and the retention layer are bonded together, either sonically or by any other suitable type of bonding. An example of suitable material for the top and bottom carrier layers is 0.3 osy (ounces per square yard) polypropylene that is 61% necked and 45% creped. Necked or neck-stretched materials are materials that have been elongated, generally in a longitudinal, or machine direction, to reduce their width in a controlled manner to a desired amount. The controlled stretching may take place under cool, room temperature or greater temperatures, and the increase in overall dimension in the direction being stretched can be limited to an amount that is less than the elongation required to break the fabric, which in most cases is about 1.2 to 1.4 times the original unstretched length. When relaxed, the web can retract toward its original dimensions. Processes for necking nonwoven materials are described in U.S. Pat. Nos. 4,443,513; 4,965,122; 4,981,747; 5,114,781; and 5,244,482 (incorporated by reference herein).

Creping involves another form of nonwoven material handling. Essentially, the creping process involves coating a nonwoven fabric with a lubricant and then pressing the coated fabric between a drive roll and a plate having a rough sandpaper-like surface. The nonwoven fabric is crinkled in a wavelike fashion in the direction of movement of the fabric by the frictional force caused by the pressing. One technique of creping is taught, for example, in U.S. Pat. No. 4,810,556, issued to Kobayashi et al., hereby incorporated by reference.

Examples of suitable neckable materials include porous nonwoven materials such as, for example, spunbonded web, meltblown web or bonded carded web. If the neckable material is a web of meltblown fibers, it may include meltblown microfibers. The neckable material may be made of fiber forming polymers such as, for example, polyolefins. Exemplary polyolefins include one or more of polypropylene, polyethylene, ethylene copolymers, propylene copolymers, and butene copolymers. Useful polypropylenes include, for example, polypropylene available from the ExxonMobil Chemical Company under the trade designation Exxon 3445, and polypropylene available from Shell Chemical Company under the trade designation DX 5A09.

Alternatively, the neckable web may be a multilayer material having, for example, at least one layer of spunbonded web joined to at least one layer of meltblown web, bonded carded web or other suitable material. For example, neckable material may be a multilayer material having a first layer of spunbonded polypropylene having a basis weight from about 0.2 to about 8 ounces per square yard (osy) (about 6.8–270 grams/m$^2$, or gsm), a layer of meltblown polypropylene having a basis weight from about 0.2 to about 4 osy (6.8–135 gsm), and a second layer of spunbond polypropylene having a basis weight of about 0.2 to about 8 osy (6.8–270 gsm). Other examples of suitable materials for the top and bottom carrier layers include vertical extrusion stranded through air bonded carded webs (TABCW) and creped spunbond.

The absorbent structure can also include a surge layer 53 (shown in FIG. 2) to improve the distribution of fluid over the absorbent core 28. The surge layer 53 can be a stranded bonded carded web (BCW) material that includes one layer of bonded carded web adhesively attached to another layer of bonded carded web. The surge layer 53 can also be provided by other structures known in the art such as combining a high wicking meltblown material or a tissue layer with a bonded carded web.

The continuous elastic absorbent core 28 includes a continuous coform layer for distribution and storage of fluid and a retention layer for storage of fluid. The continuous coform layer is formed by coforming pulp and superabsorbent particles with meltblown fibers of an elastic material. The elastic absorbent cores 28 of the invention are "continuous" in the sense that the layers that form the core 28 are unitary in the longitudinal direction 38 of the core. In a desired aspect, the core 28 is not formed of layers that are broken into segments. An example of a suitable continuous coform layer material is a co-form material including 50% Favor 880 superabsorbent material, 40% eucalyptus pulp and 10% KRATON elastomeric resin. An example of a suitable retention layer material is a material including 75% Favor 880 superabsorbent material, 10% pulp and 15% KRATON elastomeric resin. KRATON is a trade designation for products available from KRATON Polymers, Inc. with representatives in Houston, Tex.

The continuous coform and retention layers of the absorbent core 28 can be made elastic by the incorporation of elastic materials into the superabsorbent/fluff matrix. The selected elastomer (elastic material) can be meltblown, and can be introduced and incorporated as the superabsorbent/fluff matrix is formed. In addition to KRATON elastomeric resin, other suitable elastic materials that can provide elasticity to the absorbent core 28 are metallocene catalyzed polyolefin polymers. Other suitable elastic materials can include elastic materials that can be thermoplastically processed. The elastic absorbent core 28 layers of the invention can each include less than about 25% of an elastic material. Desirably, the absorbent core 28 layers can each include from about 10 to about 20% by weight of elastic material. More specifically, the absorbent core 28 layers can each include from about 13 to about 17% by weight of elastic material. In particular aspects, the elastic material can be at least a minimum of about 10 percent by weight. The elastic material can alternatively be at least about 13 percent by weight of the individual absorbent core 28 layers. In other aspects, the elastic material can be not more than a maximum of about 25 percent by weight of each layer of the absorbent core 28. The elastic material can alternatively be not more than about 20, and optionally, can be not more than about 17 percent by weight of each layer of the absorbent core 28.

The continuous elastic absorbent cores 28 of the invention can extend or elongate from about 80 to about 400 percent upon application of a force of from about 60 to about 325 grams. More particularly, the elastic absorbent cores 28 of the invention can extend or elongate from about 80 to about 400 percent upon application of a force of from about 100 to about 250 grams. Achievement of this magnitude of extension (or elongation) upon application of such relatively low forces results in low tension elastic absorbent cores 28. It is desirable to provide low tension elastic components in absorbent articles. Low tension elastic components provide a more comfortable, better fitting absorbent article. Low tension materials also make the article easier to apply because the article lays flatter and does not have a tendency to curl up. Low tension materials provide absorbent articles that are less irritating to the skin of the wearer and that better perform their absorbent function (because the absorbent materials can more closely conform to the body of the wearer). In particular aspects, the force to bring about the desired elongation can be at least a minimum of about 60 grams. The force can alternatively be at least about 80 grams and optionally, can be at least about 100 grams. In other aspects, the force to bring about the desired elongation can be not more than a maximum of about 325 grams. The force can alternatively be not more than about 250 grams. The elastic absorbent cores 28 of the invention have tensions that are substantially lower than previously described absorbent cores containing higher quantities of elastic materials. A comparison of the tensions of prior art absorbent cores with the tensions of the absorbent cores 28 of the invention is provided in Table 1. below.

TABLE 1

| Sample | Tension (grams) |
| --- | --- |
| Prior Art Absorbent Core containing 30% KRATON elastic material | 360 |
| Prior Art Absorbent Core containing 40% KRATON elastic material | 650 |
| Absorbent Core of the Invention containing 10% KRATON elastic material | 83 |
| Absorbent Core of the Invention containing 15% KRATON elastic material | 96 |

The tension of the absorbent cores was measured by placing samples of the absorbent cores within a SINTECH tensile testing machine and pulling the sample to an elongation of 180% of the original length. The value (or load) at break is a measure of the strength (or tension) of the material. The SINTECH tensile testing machine (such as Model 500/S) is available from MTS Systems Corporation, a business having offices in Research Triangle Park, N.C. The sample size of the "prior art" absorbent cores was 1 inch (2.54 cm) in the machine direction by 2 inches (5.08 cm) in the cross-direction. The sample width actually tested in the SINTECH tensile testing machine was 1 inch and the sample was elongated in the cross-direction (the SINTECH tensile testing machine was operated at a crosshead speed of 12 inches/minute). The sample size of the absorbent cores of the invention was 2 inches (5.08 cm) in the machine direction by 4 inches (10.16 cm) in the cross-direction; the area of material tested in jaws of the SINTECH tensile testing machine was 1 inch (2.54 cm) in the machine direction and 2 inches (5.08 cm) in the cross-direction. The samples of the absorbent cores of the invention were elongated in the cross-direction. The tension values measured for the prior art absorbent cores were doubled to account for the difference in the cross-direction of the tested sample area. Both the prior art and present invention samples were placed centered in the jaws of the SINTECH tensile testing machine with the cross-direction dimension being tested. The SINTECH tensile testing machine was set to have a break sensitivity of 40% and to pull the sample at a rate of 12 inches per minute.

Some "elastic" materials are capable of completely or essentially completely retracting 100% to their original length or width when the force causing their elongation is removed. Other "elastic" materials do not completely retract and remain longer or wider than their original dimension after removal of force. The continuous elastic absorbent cores 28 of the invention recover no more than about 80% of an original dimension upon relaxation of the extension or elongation force within a relatively short period of time (approximately a minute). Elastic absorbent cores 28 used in absorbent articles such as diapers are typically extended/elongated by the wearer or caregiver during application of the article; after the article is stretched for application and once the article is positioned on and secured to the wearer, the person applying the force lets go and the elastic materials are given the opportunity to retract. Typically, the materials will retract to providing a conforming fit on the wearer. With the absorbent cores 28 of the invention, the retraction is incomplete; no more than about 80% of the original dimension is recovered within a relatively short period of time (within approximately less than a minute). This means that the absorbent cores 28 of the invention can have a "set" or more or less permanent deformation of at least about 20%. For example, if an absorbent core 28 having this feature is initially about 5 inches long and is stretched 100% to a length of 10 inches, the absorbent core 28 will not completely retract to 5 inches. Instead, the "retracted" absorbent core 28 will have a length of at least about six inches. This incomplete retraction can be desirable in an absorbent article because it can lead to a better conforming and better fitting article. Incomplete recovery of a length or width dimension can result in an article that "hugs" the wearer and provides a more custom-fitting article.

In addition to being continuous and unitary, the continuous coform and retention layers of the absorbent core 28 can have a tension reducing geometry in the crotch section 26 of the diaper 20. The purpose of modifying the geometry of the absorbent core 28 in the crotch section 26 to have lower tension is to further achieve the benefits associated with low tension as described herein. In one aspect, the tension in the crotch section 26 can be reduced by providing slits or openings in the absorbent core 28. The slits or openings can be configured to not interfere with the intake, absorption and retention functions of the absorbent core 28. The slits or openings can be oriented in either the longitudinal 38 or lateral 40 direction and can have a length of from about 0.125 inches to about 2 inches. In another aspect, the tension in the crotch section 26 can be reduced by narrowing the width of the absorbent core 28. For example, the width of the absorbent core 28 in the crotch section 26 can be reduced by about 5 to about 75 percent to reduce tension.

The elastic absorbent cores 28 of the invention can retain their integrity after fluid loading, thereby improving their use and performance in absorbent articles. Conventional absorbent cores tend to become disrupted and lose their integrity when wet. Typically, the dry tensile strength of an absorbent core is significantly higher than the wet tensile strength of an absorbent core. The continuous elastic absorbent cores 28 of the invention have a wet tensile strength that is at least 95% of the dry tensile strength. In fact, testing of the absorbent cores 28 of the invention has even shown wet tensile strengths higher than the dry tensile strengths. The dry and wet tensile strengths of a conventional absorbent core and of samples representing the continuous coform and retention layers of the absorbent cores 28 of the invention were measured. The dry and wet tensile strengths were measured by testing 2 inch (5.08 cm) (in the machine direction) by 4 inch (10.16 cm) (in the cross-direction) samples of the absorbent cores in a SINTECH tensile testing machine. A crosshead speed of 12 inches/min (30.48 cm/min) and a gage length of one inch were used. In order to prepare the wet tensile strength samples, the cores were soaked in 2% $CaCl_2$ solution for 20 minutes prior to testing. The samples were secured in the grips of the SINTECH tensile testing machine. The SINTECH tensile testing machine program is initiated and the peak load is measured. The dry and wet tensile strengths are provided in Table 2. below.

TABLE 2

| Sample | Dry Tensile Strength (grams) | Wet Tensile Strength (grams) | Wet Tensile Strength/Dry Tensile Strength |
|---|---|---|---|
| HUGGIES ULTRATRIM diaper absorbent core | 544.8 | 0 | 0 |
| Continuous Coform layer of absorbent core of the invention (50% superabsorbent; 40% pulp; 10% KRATON elastomeric resin) | 227.0 | 272.0 | 1.2 |
| Retention layer of absorbent core of the invention (75% superabsorbent; 10% pulp; 15% KRATON elastomeric resin) | 272.0 | 317.8 | 1.2 |

The HUGGIES ULTRATRIM diaper absorbent core was a 40:60 superabsorbent/fluff combination densified to 0.2 $g/cm^3$. The HUGGIES diaper absorbent core had the longer sample dimension (4 inches) in the machine direction and the sample was pulled in the machine direction. The samples representing the layers of absorbent cores of the invention were made from Stockhausen SXM 880 superabsorbent; Sulfatate HJ pulp; and KRATON WTC-98-0253 for the continuous coform layer and KRATON G 2740 for the retention layer. The samples representing the layers of absorbent cores of the invention had their longer dimension (4 inches) in the cross-direction and the samples were pulled in the cross-direction. For all of the samples, the tested area between the grips of the SINTECH tensile testing machine was about 1 inch by 2 inches. The test results provided in Table 2. show that the absorbent cores 28 of the invention have improved integrity when wet. The absorbent cores 28 of the invention can be expected to have wet tensile strengths that are approximately equal to, if not greater than, the dry tensile strength of the cores. The improved wet integrity of the absorbent cores 28 of the invention translates to better fitting and better performing absorbent articles.

Figure 3:
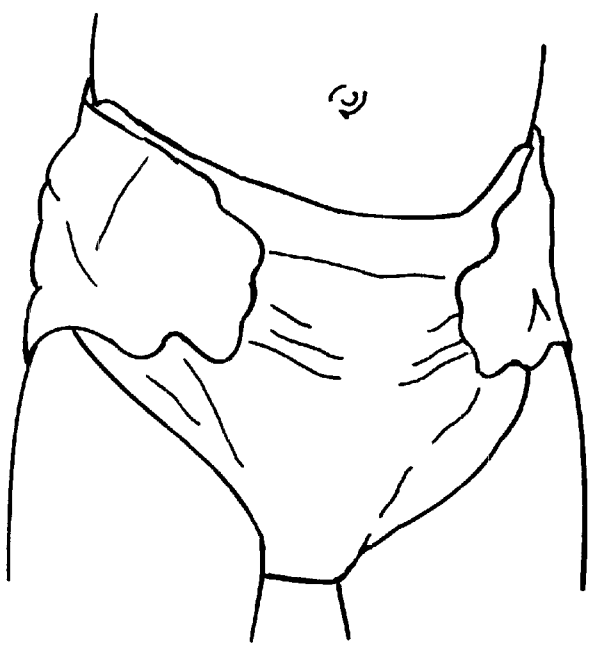
FIGS. 3 and 3A are drawings based on front and side view photographs of a child wearing a diaper having a conventional absorbent core.
Figure 3A:
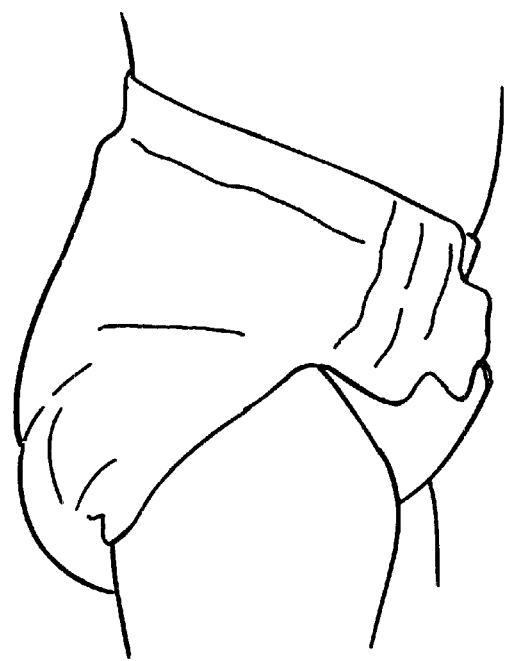
Figure 4:
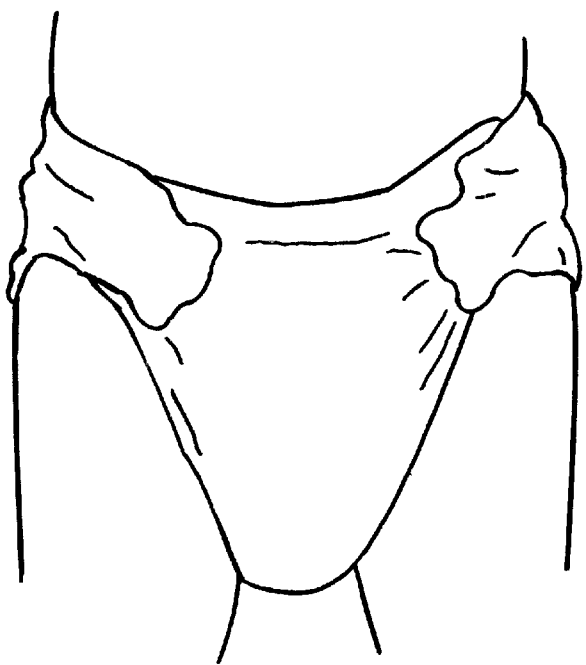
FIGS. 4 and 4A are drawings based on front and side view photographs of a child wearing the diaper of FIGS. 3 and 3A after loading of the diaper until leakage occurred.
Figure 5:
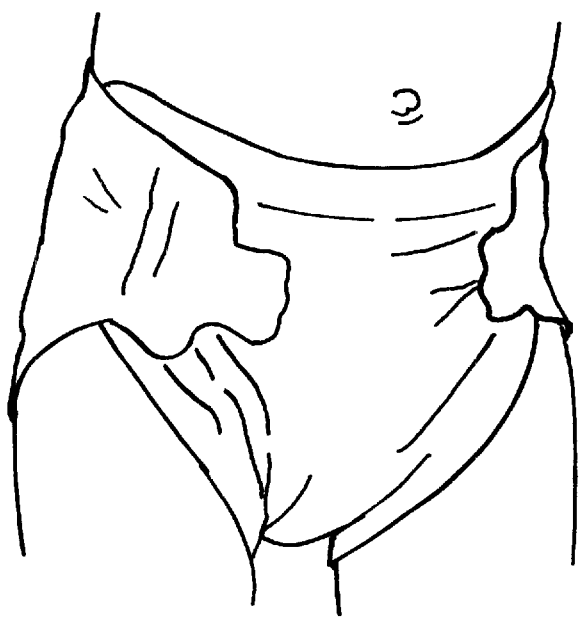
FIGS. 5 and 5A are drawings based on front and side view photographs of a child wearing a diaper having a continuous elastic absorbent core of the invention.
Figure 5A:
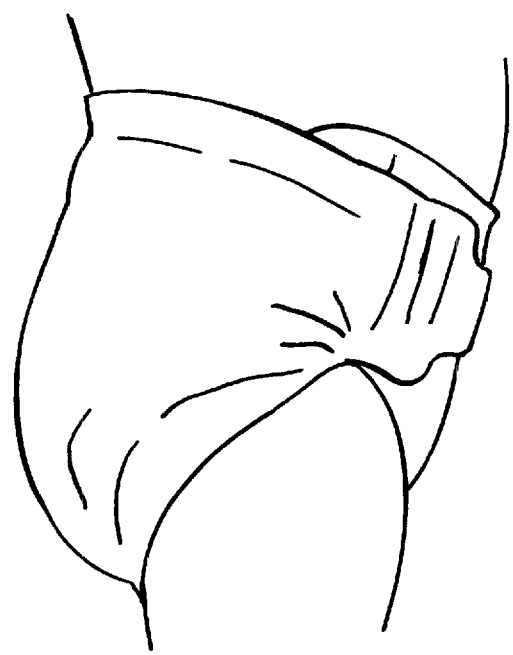
Figure 6:
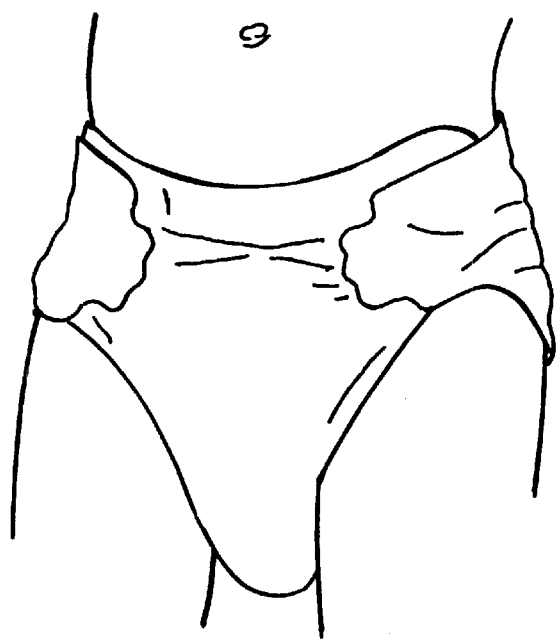
FIGS. 6 and 6A are drawings based on front and side view photographs of a child wearing the diaper of FIG. 5 after loading of the diaper until leakage occurred.

The improvements in fit and performance of the elastic absorbent cores 28 of the invention are visible by comparing photographs taken of diapers having and not having the absorbent cores 28 of the invention. Photographs were taken of toddlers wearing various diapers during a forced leakage (or "failure") study; that is, the general purpose of the study was to study the performance of the diapers by loading the diapers until they leaked. FIGS. 3–6 are drawings made from photographs taken of the same child wearing a diaper not having an elastic absorbent core (FIGS. 3 and 4), and a diaper having an elastic absorbent core 28 of the invention (FIGS. 5 and 6). FIGS. 3 and 5 show the diapers before the forced failure test, and FIGS. 4 and 6 show the diapers after the forced failure test. The diapers tested (with and without elastic absorbent core) were similarly constructed except for the absorbent cores; both diapers were constructed with biaxially stretchable outer cover material.

Figure 4A:
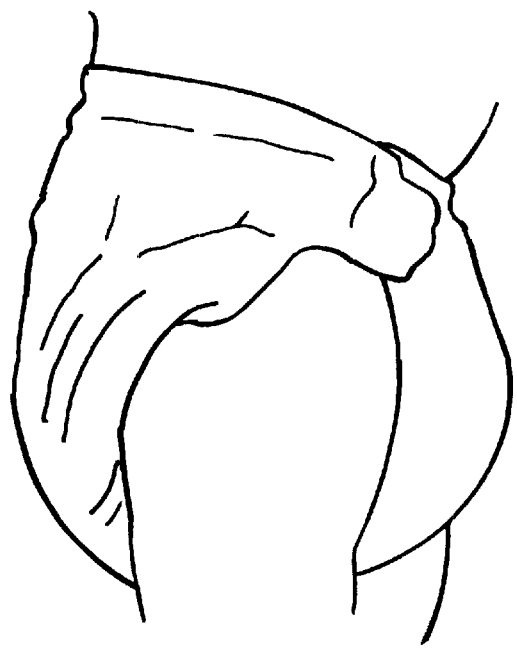
Figure 6A:
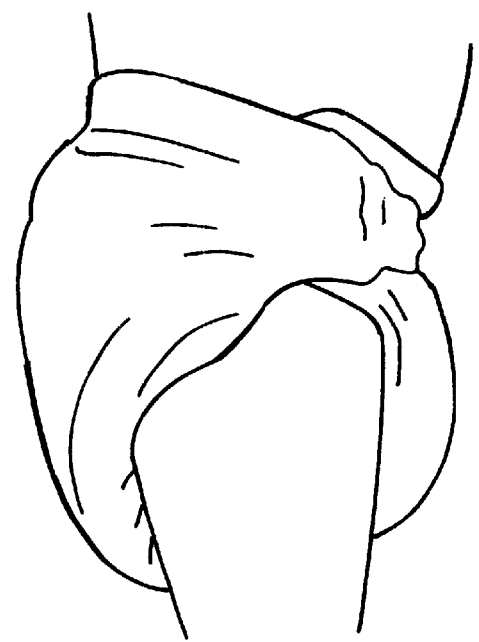

FIGS. 3 and 5 show a comparison of the different diapers prior to the forced leakage. Even before loading, the diaper of FIG. 5 appears to be better-fitting and more closely conforms to the body shape of the child. The diaper of FIG. 5 has less bunched material in the crotch section and front waist section and the fasteners appear to be more securely attached to the front waist section of the diaper. FIGS. 4 and 6 show a comparison of the diapers after the forced leakage. The difference in the performance of the two diapers is more visible in the drawings based on the side view (FIGS. 4A and 6A) photographs. Even though loaded with liquid in an amount that is far greater than the loading experienced by diapers in normal use, the diaper of FIG. 6 has sufficiently retained its general profile. In contrast, the diaper of FIG. 5 is bulged out substantially more in the front and back waist sections. Further, it appears that the diaper of FIG. 6 maintained a better seal in the leg opening region. FIGS. 3–6 clearly illustrate the fit and performance benefits achieved through use of an elastic absorbent core 28 of the invention in an absorbent article.

Delivering the low tension elastic properties of the present invention in absorbent cores to be used in absorbent articles provide several benefits including improved fit and improved performance. The low tension elastic properties are also delivered cost efficiently and in such a way that the absorption capacity of the absorbent cores is not diminished substantially. The low tension and incomplete retraction properties provide absorbent articles that are better conforming and more comfortable to the wearer.

It will be appreciated that details of the absorbent cores of the invention, given for purposes of illustration, are not to be construed as limiting the scope of this invention. Although only a few exemplary aspects of this invention have been described in detail above, those skilled in the art will readily appreciate that many modifications are possible in the exemplary aspects without materially departing from the novel teachings and advantages of this invention. Accordingly, all such modifications are intended to be included within the scope of this invention, which is defined in the following claims and all equivalents thereto. Further, it is recognized that many aspects may be conceived that do not achieve all of the advantages of some aspects, particularly of the preferred aspects, yet the absence of a particular advantage should not be construed to necessarily mean that such an aspect is outside the scope of the present invention.

We claim:

1. A dynamic-fitting absorbent article comprising:
   a liquid impermeable outer cover;
   a liquid permeable bodyside liner in superimposed relation to the outer cover; and
   a continuous elastic absorbent core disposed between the outer cover and the bodyside liner wherein the continuous elastic absorbent core has a tension of from about 60 to about 325 grams when extended by about 80% of an initial length.

2. The absorbent article of claim 1 wherein the continuous elastic absorbent core has a tension of from about 60 to about 325 grams when extended by about 200% of an initial length.

3. The absorbent article of claim 1 wherein the continuous elastic absorbent core has a tension of from about 100 to about 250 grams when extended by about 100% of an initial length.

4. The absorbent article of claim 1 wherein the continuous elastic absorbent core recovers no more than about 80% of an original dimension upon relaxation of the extension force.

5. The absorbent article of claim 1 wherein the continuous elastic absorbent core has a tension reducing geometry in a crotch section of the absorbent core.

6. The absorbent core of claim 5 wherein the tension reducing geometry includes at least one slit.

7. The absorbent core of claim 5 wherein the tension reducing geometry includes the crotch section having a narrowed width.

8. The absorbent article of claim 1 wherein the continuous elastic absorbent core has a dry tensile strength, and has a wet tensile strength that is at least 95% of the dry tensile strength.

9. The absorbent article of claim 1 wherein the continuous elastic absorbent core includes from about 10 to about 20 percent of an elastic material.

10. The absorbent article of claim 1 wherein the continuous elastic absorbent core includes from about 13 to about 17 percent of an elastic material.

11. The absorbent article of claim 1 wherein the outer cover is a biaxially stretchable material.

12. The absorbent article of claim 1 wherein the outer cover is a biaxially elastic material.

13. The absorbent article of claim 1 wherein the bodyside liner is a biaxially stretchable material.

14. The absorbent article of claim 1 wherein the bodyside liner is a biaxially elastic material.

15. A dynamic-fitting absorbent article comprising:
   a liquid impermeable, biaxially stretchable outer cover;
   a liquid permeable, biaxially stretchable bodyside liner in superimposed relation to the outer cover; and
   a continuous elastic absorbent core disposed between the outer cover and the bodyside liner wherein the continuous elastic absorbent core has a tension of from about 60 to about 325 grams when extended by about 80% of an initial length.

16. The absorbent article of claim 15 wherein the continuous elastic absorbent core has a tension of from about 60 to about 325 grams when extended by about 200% of an initial length.

17. The absorbent article of claim 15 wherein the continuous elastic absorbent core has a tension of from about 100 to about 250 grams when extended by about 100% of an initial length.

18. The absorbent article of claim 15 wherein the continuous elastic absorbent core recovers no more than about 80% of an original dimension upon relaxation of the extension force.

19. The absorbent article of claim 15 wherein the continuous elastic absorbent core has a dry tensile strength and a wet tensile strength that is at least 95% of the dry tensile strength.

20. A dynamic-fitting absorbent article comprising:
   a liquid impermeable outer cover;
   a liquid permeable bodyside liner in superimposed relation to the outer cover; and
   a continuous elastic absorbent core disposed between the outer cover and the bodyside liner wherein the continuous elastic absorbent core recovers less than about 80% of an original dimension upon relaxation of an extension force and wherein the elastic absorbent core includes less than about 25% of an elastic material.

21. The absorbent article of claim 20 wherein the continuous elastic absorbent core has a tension of from about 60 to about 325 grams when extended by about 80% of an initial length.

22. The absorbent article of claim 20 wherein the continuous elastic absorbent core has a tension of from about 60 to about 325 grams when extended by about 200% of an initial length.

23. The absorbent article of claim 20 wherein the continuous elastic absorbent core has a tension of from about 100 to about 250 grams when extended by about 100% of an initial length.

24. The absorbent article of claim 20 wherein the continuous elastic absorbent core has a tension reducing geometry in a crotch section of the absorbent core.

25. The absorbent core of claim 24 wherein the tension reducing geometry includes at least one slit.

26. The absorbent core of claim 24 wherein the tension reducing geometry includes the crotch section having a narrowed width.

27. The absorbent article of claim 20 wherein the continuous elastic absorbent core has a dry tensile strength and a wet tensile strength that is at least 95% of the dry tensile strength.

28. The absorbent article of claim 20 wherein the continuous elastic absorbent core includes from about 10 to about 20 percent of elastic material.

29. The absorbent article of claim 20 wherein the continuous elastic absorbent core includes from about 13 to about 17 percent of elastic material.

30. The absorbent article of claim 20 wherein the outer cover is a biaxially stretchable material.

31. The absorbent article of claim 20 wherein the outer cover is a biaxially elastic material.

32. The absorbent article of claim 20 wherein the bodyside liner is a biaxially stretchable material.

33. The absorbent article of claim 20 wherein the bodyside liner is a biaxially elastic material.

34. A dynamic-fitting absorbent article comprising:
a liquid impermeable, biaxially stretchable outer cover;
a liquid permeable, biaxially stretchable bodyside liner in superimposed relation to the outer cover; and
a continuous elastic absorbent core disposed between the outer cover and the bodyside liner wherein the continuous elastic absorbent core recovers less than about 80% of an original dimension upon relaxation of an extension force and wherein the elastic absorbent core includes less than about 25% of an elastic material.

35. The absorbent article of claim 34 wherein the continuous elastic absorbent core has a tension of from about 60 to about 325 grams when extended by about 80% of an initial length.

36. The absorbent article of claim 34 wherein the continuous elastic absorbent core has a tension of from about 60 to about 325 grams when extended by about 200% of an initial length.

37. The absorbent article of claim 34 wherein the continuous elastic absorbent core has a tension of from about 100 to about 250 grams when extended by about 100% of an initial length.

38. The absorbent article of claim 34 wherein the continuous elastic absorbent core has a dry tensile strength, and has a wet tensile strength that is at least 95% of the dry tensile strength.

39. A dynamic-fitting absorbent article comprising:
a liquid impermeable outer cover;
a liquid permeable bodyside liner in superimposed relation to the outer cover; and
a continuous elastic absorbent core disposed between the outer cover and the bodyside liner wherein the continuous elastic absorbent core recovers less than about 80% of an original dimension upon relaxation of an extension force; includes less than about 25% of an elastic material; and has a dry tensile strength, and has a wet tensile strength that is at least 95% of the dry tensile strength.

40. The absorbent article of claim 39 wherein the continuous elastic absorbent core has a tension of from about 60 to about 325 grams when extended by about 80% of an initial length.

41. The absorbent article of claim 39 wherein the continuous elastic absorbent core has a tension of from about 60 to about 325 grams when extended by about 200% of an initial length.

42. The absorbent article of claim 39 wherein the continuous elastic absorbent core has a tension of from about 100 to about 250 grams when extended by about 100% of an initial length.

43. The absorbent article of claim 39 wherein the continuous elastic absorbent core has a tension reducing geometry in a crotch section of the absorbent core.

44. The absorbent core of claim 43 wherein the tension reducing geometry includes at least one slit.

45. The absorbent core of claim 43 wherein the tension reducing geometry includes the crotch section having a narrowed width.

46. The absorbent article of claim 39 wherein the continuous elastic absorbent core includes from about 10 to about 20 percent of elastic material.

47. The absorbent article of claim 39 wherein the continuous elastic absorbent core includes from about 13 to about 17 percent of elastic material.

48. The absorbent article of claim 39 wherein the outer cover is a biaxially stretchable material.

49. The absorbent article of claim 39 wherein the outer cover is a biaxially elastic material.

50. The absorbent article of claim 39 wherein the bodyside liner is a biaxially stretchable material.

51. The absorbent article of claim 39 wherein the bodyside liner is a biaxially elastic material.

52. A dynamic-fitting absorbent article comprising:
a liquid impermeable, biaxially stretchable outer cover;
a liquid permeable, biaxially stretchable bodyside liner in superimposed relation to the outer cover; and
a continuous elastic absorbent core disposed between the outer cover and the bodyside liner wherein the continuous elastic absorbent core recovers less than about 80% of an original dimension upon relaxation of an extension force; includes less than about 25% of an elastic material; and has a dry tensile strength, and has a wet tensile strength that is at least 95% of the dry tensile strength.

53. The absorbent article of claim 52 wherein the continuous elastic absorbent core has a tension of from about 60 to about 325 grams when extended by about 80% of an initial length.

54. The absorbent article of claim 52 wherein the continuous elastic absorbent core has a tension of from about 60 to about 325 grams when extended by about 200% of an initial length.

55. The absorbent article of claim 52 wherein the continuous elastic absorbent core has a tension of from about 100 to about 250 grams when extended by about 100% of an initial length.

56. A dynamic-fitting absorbent article comprising:
a liquid impermeable outer cover;
a liquid permeable bodyside liner in superimposed relation to the outer cover; and
a continuous elastic absorbent core disposed between the outer cover and the bodyside liner wherein the continuous elastic absorbent core has a tension of from about 60 to about 325 grams when extended by about 200% of an initial length.

57. A dynamic-fitting absorbent article comprising:
a liquid impermeable outer cover;
a liquid permeable bodyside liner in superimposed relation to the outer cover; and
a continuous elastic absorbent core disposed between the outer cover and the bodyside liner wherein the continuous elastic absorbent core has a tension of from about 60 to about 325 grams when extended by about 300% of an initial length.

58. A dynamic-fitting absorbent article comprising:
a liquid impermeable outer cover;
a liquid permeable bodyside liner in superimposed relation to the outer cover; and
a continuous elastic absorbent core disposed between the outer cover and the bodyside liner wherein the continuous elastic absorbent core has a tension of from about 60 to about 325 grams when extended by about 400% of an initial length.

* * * * *